United States Patent [19]

Matsumoto et al.

[11] Patent Number: 4,482,493
[45] Date of Patent: Nov. 13, 1984

[54] METHOD FOR PREPARING BENZOQUINONES

[75] Inventors: Masakatsu Matsumoto, Sagamihara, Japan; Satoru Ito, Rockville, Md.

[73] Assignee: Sagami Chemical Research Center, Tokyo, Japan

[21] Appl. No.: 542,975

[22] Filed: Oct. 18, 1983

[30] Foreign Application Priority Data

Oct. 22, 1982 [JP] Japan ................................. 57-184684
Feb. 28, 1983 [JP] Japan ................................. 58-30744
Aug. 2, 1983 [JP] Japan ................................. 58-140615

[51] Int. Cl.³ ............................................. C07C 50/04
[52] U.S. Cl. ............................................. 260/396 R
[58] Field of Search .................... 260/396 R; 502/162, 502/174, 226, 230

[56] References Cited

U.S. PATENT DOCUMENTS

| | | | |
|---|---|---|---|
| 2,395,638 | 2/1946 | Milas | 260/396 R |
| 3,012,043 | 12/1961 | Dowden et al. | 260/396 R |
| 3,193,584 | 7/1965 | Rylander et al. | 502/174 |
| 3,670,034 | 6/1972 | Robinson | 260/396 R |
| 3,671,552 | 6/1972 | LeBris et al. | 260/396 R |
| 3,833,634 | 9/1974 | Pruett et al. | 502/174 |

OTHER PUBLICATIONS

Patai, *The Chemistry of the Hydroxyl Group*, part 1, 1971, pp. 505-592.

*Primary Examiner*—Alton D. Rollins
*Assistant Examiner*—Raymond Covington
*Attorney, Agent, or Firm*—Oblon, Fisher, Spivak, McClelland & Maier

[57] ABSTRACT

A method for preparing a benzoquinone represented by the general formula:

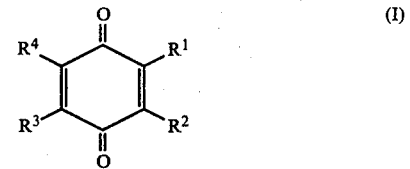

where each of $R^1$, $R^2$, $R^3$ and $R^4$ is a hydrogen atom, an alkyl group or an aryl group, which comprises reacting a phenol represented by the general formula:

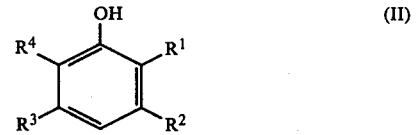

where $R^1$, $R^2$, $R^3$ and $R^4$ are as defined above, with hydrogen peroxide in the presence of a ruthenium catalyst.

16 Claims, No Drawings

METHOD FOR PREPARING BENZOQUINONES

The present invention relates to a method for preparing benzoquinones represented by the general formula:

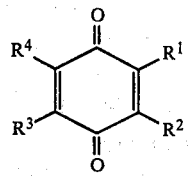
(I)

where each of $R^1$, $R^2$, $R^3$ and $R^4$ is a hydrogen atom, an alkyl group, or an aryl group. More particularly, the present invention relates to a method for preparing the benzoquinones of the general formula I by reacting phenols represented by the general formula:

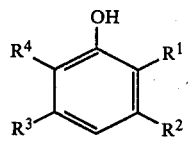
(II)

where $R^1$, $R^2$, $R^3$ and $R^4$ are as defined above, with hydrogen peroxide.

The benzoquinones of the general formula I are widely used as perfumes, pharmaceuticals or starting materials thereof.

Heretofore, as methods for preparing the benzoquinones of the general formula I directly from the phenols of the general formula II, there have been known a reagent-oxidation method employing (a) a Fremy's salt i.e. a nitrosodisulfonate [Shin Jikken Kagaku Koza, 15, published by Maruzen (1976)], (b) manganese dioxide [R. Michel, German Laid-open Patent Publication 2502332 (1975)], or (c) a thallium salt [Shin Jikken Kagaku Koza, 15, published by Maruzen (1976)]; (d) an oxygen-oxidation method employing a cobalt-Schiff base complex [Shin Jikken Kagaku Koza, 15, published by Maruzen (1976)]; (e) a basic spontaneous oxidation method [Shin Jikken Kagaku Koza, 15, published by Maruzen (1976)]; and (f) an oxygen-oxidation in the presence of copper (II) salts [R. A. Sheldon and J. K. Kochi, "Metal-Catalyzed Oxidations of Organic Compounds" Academic Press, New York, 1981, P368]. However, the method (a) is hardly applicable as an industrial method because of the difficulties in the stability of the Fremy's salt and in the mass production. The methods (b) and (e) are also hardly applicable for an industrial process because of difficulties such that the reagents must be used stoichiometrically and that the after-treatment is cumbersome. The method (c) has a problem in that thallium is poisonous. The method (d) has not yet been industrially employed because the Schiff's base is too expensive. The method (f) requires at least a stoichiometric amount of the copper salt and the reaction is required to be conducted in an oxygen atmosphere under high pressure.

The present inventors have conducted an extensive research to overcome the difficulties of the conventional methods and have finally found an industrial method whereby substituted phenols can readily be converted to the corresponding benzoquinones in good yield. The present invention is based on this discovery.

Namely, the present invention provides a method for preparing a benzoquinone represented by the general formula:

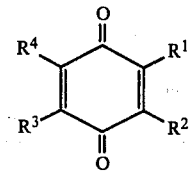
(I)

where each of $R^1$, $R^2$, $R^3$ and $R^4$ is a hydrogen atom, an alkyl group, or an aryl group, which comprises reacting a phenol represented by the general formula:

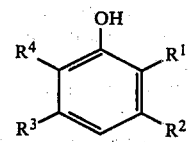
(II)

where $R^1$, $R^2$, $R^3$ and $R^4$ are as defined above, with hydrogen peroxide in the presence of a ruthenium catalyst.

Now, the present invention will be described in detail with reference to the preferred embodiments.

As the phenol of the general formula II to be used as a starting material in the present invention, there may be mentioned cresol, xylenol, trimethyl phenol, tetramethyl phenol or phenyl phenol. As the hydrogen peroxide, there may be used a commercial product normally available in the form of an aqueous solution. The aqueous solution containing about 30% of hydrogen peroxide is preferably used.

According to the present invention, the reaction is conducted in the presence of a ruthenium catalyst.

As the ruthenium catalyst, there may be used ruthenium chloride, ruthenium bromide, a $\mu_3$-oxotriruthenium complex, a ruthenium phosphine complex such as tris-triphenylphosphine ruthenium dichloride or tris-triphenylphosphine ruthenium hydride, and a ruthenium carbonyl complex.

The catalyst may be used as a homogeneous catalyst system or as a heterogeneous catalyst system wherein the ruthenium catalyst is supported on an inert carrier such as silica gel, alumina, diatomaceous earth or active carbon.

In a preferred embodiment of the present invention, the ruthenium catalyst is supported on a carrier together with an alkaline earth metal. With use of such a catalyst system, secondary reactions of the formed benzoquinone and hydroquinone can be suppressed, whereby the benzoquinones are obtainable in good yield. The ruthenium catalyst as mentioned above is supported on a carrier in a reduction supporting method commonly employed in this particular technical field. The amount of ruthenium to be supported is usually from 0.5 to 20% by weight, based on the carrier used.

As the alkaline earth metal to be supported on the carrier together with the ruthenium catalyst, there may be mentioned magnesium, calcium, strontium and barium. The alkaline earth metal is supported on the carrier by impregnation treatment with its hydroxide, acetate or chloride. The amount of the alkaline earth metal to be supported is usually from 0.02 to 2 equivalent, based on ruthenium.

The catalyst system may be prepared by firstly supporting the above-mentioned ruthenium compound on a carrier and then supporting the alkaline earth metal thereon. However, it may also be prepared by supporting the alkaline earth metal on a commercial product of ruthenium-active carbon.

The reaction of the present invention is preferably carried out in a solvent. As the solvent, there may be used a carboxylic acid such as acetic acid or formic acid, or a mixture of a saturated alcohol such as methanol or ethanol, with a mineral acid such as hydrochloric acid.

In another preferred embodiment of the present invention, the reaction is carried out in a medium composed essentially of from 50 to 99.5% by weight of acetic acid and from 0.5 to 50% by weight of another acid having a smaller acid dissociation index (pKa) than acetic acid, whereby it is possible to prevent side reactions to form a dimer or hydroquinone, and to facilitate the reaction to obtain the benzoquinones in extremely good yield. As the acid having a smaller acid dissociation index (pKa) than acetic acid, there may be mentioned a carboxylic acid such as formic acid, oxalic acid, malonic acid, methoxyacetic acid, chloroacetic acid, dichloroacetic acid, trichloroacetic acid, trifluoroacetic acid or benzoic acid; a sulfonic acid such as methanesulfonic acid, benzenesulfonic acid or toluenesulfonic acid; and a mineral acid such as hydrochloric acid or sulfuric acid.

The reaction of the present invention proceeds within a temperature range of from 0° to 100° C. However, in order to obtain the desired product in good yield, it is preferred to conduct the reaction at a temperature of from 10° to 60° C., more preferably from 20° to 60° C.

The catalyst of the present invention may be used repeatedly.

Now, the present invention will be described with reference to Examples. However, it should be understood that the present invention is by no means restricted by these specific Examples.

EXAMPLE 1

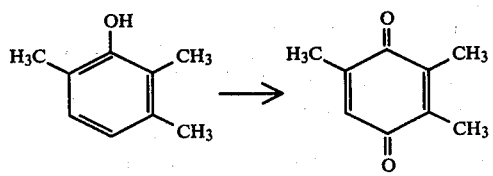

500 mg of 2,3,6-trimethylphenol and 10 mg of $RuCl_3 \cdot 3H_2O$ were dissolved in 5 ml of acetic acid, and 1 g of 30% hydrogen peroxide was dropwise added to the solution at room temperature. The mixture was stirred for 5 hours. (In some cases, a dimer precipitates in the reaction solution (from 0 to 10%), but it can readily be removed by filtration.) After adding a small amount of a sodium thiosulfate solution, the reaction mixture was extracted with ether. The ether layer was dried over magnesium sulfate and subjected to distillation under reduced pressure to remove the ether. The residue was purified by a silica gel column (by using methylene chloride as the eluent), whereby 496 mg (90% yield) of 2,3,6-trimethylbenzoquinone was obtained. The physical properties of the trimethylbenzoquinone corresponded to those values identified in the literature [Shin Jikken Kagaku Koza, 15, published by Maruzen 1976].

EXAMPLE 2

The reaction and after-treatment were carried out in the same manner as in Example 1 except that 10 mg of $Ru(H)OCOCH_3(PPh_3)_3$ was used instead of $RuCl_3 \cdot 3H_2O$, whereby 200 mg of unreacted starting material and 200 mg (61% yield) of trimethylbenzoquinone were obtained.

EXAMPLE 3

The reaction and after-treatment were carried out in the same manner as in Example 1 except that 30 mg of 5% ruthenium-carbon was used instead of $RuCl_3 \cdot 3H_2O$, whereby 435 mg (79% yield) of trimethyl-benzoquinone was obtained.

EXAMPLE 4

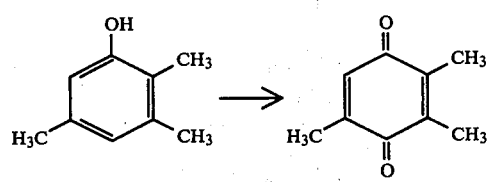

500 mg of 2,3,5-trimethylphenol and 10 mg of $RuCl_3 \cdot 3H_2O$ was reacted in 5 ml of acetic acid in the same manner as in Example 1, followed by the same treatment as in Example 1, whereby 100 mg of unreacted starting material and 230 mg (51% yield) of trimethylbenzoquinone was obtained.

EXAMPLE 5

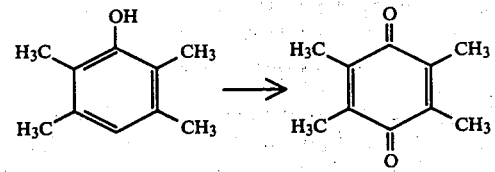

500 mg of 2,3,5,6-tetramethylphenol and 10 mg of $RuCl_3 \cdot 3H_2O$ were reacted in 5 ml of acetic acid in the same manner as in Example 1, followed by the same treatment as in Example 1, whereby 288 mg (53% yield) of tetramethylbenzoquinone and 228 mg of a mixture of three unidentified substances were obtained. The tetramethylbenzoquinone was recrystallized from hexane to obtain yellow needle-like crystals having a melting point of from 114° to 115° C.

Mass spectrum: m/e 164 (M+, 94), 136(65), 121(100).
Infrared spectrum: $\nu_{c=o}$ 1634 cm$^{-1}$

EXAMPLE 6

In an argon gas atmosphere, 1 g of 5% ruthenium-carbon powder (Lot. No. 548 manufactured by Nippon Engelhard Co.) was added to 15 ml of an aqueous solution containing 31 mg of barium hydroxide, and the mixture was refluxed for 2 hours. After cooling, the mixture was filtered, and the carbon powder was washed with water until the filtrate became neutral and dried under reduced pressure at room temperature. The catalyst thereby obtained was subjected to X-ray fluorometric analysis, whereby the characteristic spectrum intensity Ba(Lα)/Ru(Kα) was 0.36.

EXAMPLE 7

500 mg of 2,3,6-trimethylphenol and 30 mg of the catalyst prepared in Example 6 were added to 5 ml of acetic acid, and 1 g of a 30% hydrogen peroxide aqueous solution was further added at room temperature. The mixture was stirred for 6 hours. After the completion of the reaction, the catalyst was removed by filtration, and the acetic acid solution was washed with an aqueous solution of NaHCO₃ and extracted with ether. After drying over MgSO₄, the solution was concentrated, and the residue was eluted through a silica gel column with dichloromethane, whereby 515 mg (94% yield) of trimethylbenzoquinone was obtained. The physical properties of the product (yellow needle-like crystals as crystallized from hexane, having a melting point of 28° C.) corresponded to the values identified in the literature [Org. Syn. 52, 83 (1972)].

EXAMPLE 8

600 mg of the catalyst prepared in Example 6 and 10 g of 2,3,6-trimethylphenol were added to 90 ml of acetic acid. While cooling the solution with ice water, 20 g of a 30% hydrogen peroxide aqueous solution was dropwise added in about 40 minutes, and the mixture was stirred overnight. After completion of the reaction, the catalyst was removed by filtration, and the acetic acid solution was concentrated under reduced pressure to about 20 ml, diluted with ether, washed with an aqueous solution of NaHCO₃ and then dried. The ether was distilled off, and the residue was subjected to distillation under reduced pressure, whereby 8.7 g of trimethylbenzoquinone (boiling point: 64° C./0.7 torr) was obtained. Further, the distillation residue was treated by column chromatography (SiO₂/CH₂Cl₂), whereby 0.5 g of trimethylbenzoquinone was additionally obtained. The total amount was 9.2 g (84% yield).

EXAMPLES 9 TO 13

The reactions were conducted at room temperature by using 500 mg of 2,3,6-trimethylphenol, 5 ml of acetic acid, 1 g of a 30% hydrogen peroxide aqueous solution, and 30 mg of a Ru-Ba/C catalyst prepared in the same manner as in Example 6 except that the concentration of the barium hydroxide was varied. The results thereby obtained are shown in Table 1.

In Table 1, the results obtained by Example 7 are also presented.

TABLE 1

|  | Ba(mmol)* | Ba(Lα)/Ru(Kα) | Trimethylbenzo-quinone (yield: %) |
|---|---|---|---|
| Example 9 | 0.07 | — | 88 |
| Example 10 | 0.15 | — | 89 |
| Example 7 | 0.18 | 0.36 | 94 |
| Example 11 | 0.22 | — | 91 |
| Example 12 | 0.36 | 0.67 | 92 |
| Example 13 | 0.54 | 0.89 | 86 |

*The amount of used Ba(OH)₂ per 1 g of 5% Ru—C.

EXAMPLE 14

Trimethylphenol was oxidized in the same manner as in Example 7 by using a Ru-Ca/C catalyst prepared in the same manner as in Example 6 except that 46 mg of calcium hydroxide was used instead of 31 mg of barium hydroxide, whereby trimethylbenzoquinone was obtained in 84% yield.

EXAMPLES 15 TO 17

2,3,6-Trimethylphenol was oxidized in the same manner as in Example 7 by using 30 mg of a ruthenium-alkaline earth metal/carbon catalyst prepared in the same manner as in Example 6 except that instead of 0.18 mmols (31 mg) of barium hydroxide, the same molar amount of calcium hydroxide, strontium acetate or magnesium acetate was used, whereby trimethylbenzoquinone was obtained in the yields identified in Table 2.

TABLE 2

|  | Alkaline earth metal salt | Trimethylbenzo-quinone (yield: %) |
|---|---|---|
| Example 15 | Ca(OH)₂ | 89 |
| Example 16 | Sr(OAc)₂ | 89 |
| Example 17 | Mg(OAc)₂ | 87 |

EXAMPLE 18

The reaction and after-treatment were conducted in the same manner as in Example 7 except that 500 mg of 2,3,5,6-tetramethylphenol was used instead of 500 mg of 2,3,6-trimethylphenol, whereby tetramethylbenzoquinone was obtained in 55% yield.

EXAMPLE 19

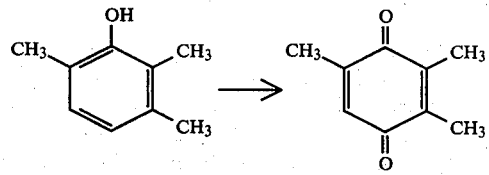

In an argon gas atmosphere, 138 mg of barium hydroxide octahydrate was dissolved in 15 ml of methanol, and 2 g of 5% ruthenium-carbon powder (Lot. No. 643 manufactured by Nippon Engelhard Co.) was added to the solution. The mixture was stirred overnight at room temperature. After removing methanol, the mixture was dried under reduced pressure at room temperature.

To 30 mg of the Ru-Ba/C catalyst thus prepared, 100 mg of water was added and stirred for 30 minutes, and then 5 ml of an acetic acid solution containing 25% of formic acid was added. Under cooling with water, 500 mg of 2,3,6-trimethylphenol and 1 g of a 31% hydrogen peroxide aqueous solution were added, and the mixture was stirred for 3 hours. After the completion of the reaction, the reaction mixture was diluted with ether, and, after adding pentamethylbenzene as an internal standard, analyzed by gas chromatography, whereby the yield of trimethylbenzoquinone was found to be 98.3%. Further, the catalyst was filtered and washed successively with an aqueous solution of NaHCO₃ and a saturated sodium chloride aqueous solution. The filtrate was dried over magnesium sulfate and then concentrated, and the residue was eluted through a silica gel column by a solvent mixture of hexane-dichloromethane (4:1), whereby 452 mg (82.1% yield) of trimethylbenzoquinone was obtained.

The physical properties of the product (yellow needle-like crystals as crystallized from hexane, having a melting point of 28° C.) corresponded to the values identified in the literature [Org. Syn., 52, 83(1972)].

The conditions for the gas chromatography employed for the analysis were as follows:
Glass column: 3% ethylene glycol adipate polyester (EGA) 1.2 m
Temperature: 100° C.

EXAMPLES 20 TO 32 AND COMPARATIVE EXAMPLES 1 TO 3

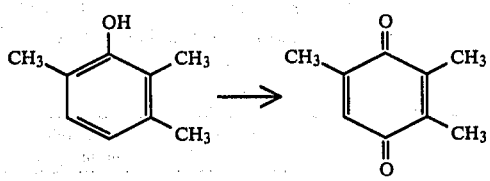

The reactions are conducted in the same manner as in Example 19 except that the compositions of the solvent and the catalyst system were varied as identified in Table 3. The results thereby obtained are also shown in the Table.

Among the catalysts used, "Ru-Ba/C" is the one prepared in Example 19, "Ru/C" is the commercial product (Lot. No. 643 manufactured by Nippon Engelhard Co.) mentioned in Example 19, and the active carbon "C" is the commercial product (Art. 2186) manufactured by Merck Co.

Examples 20 to 28 represent the preferred embodiment wherein the solvent system is composed of acetic acid with various amounts (as indicated by percentage in Table 3) of another acid having a smaller acid dissociation index (pKa) than acetic acid. Examples 29 to 32 also represent the present invention but the solvent system is outside the scope of the preferred embodiment. Comparative Examples 1 to 3 are outside the scope of the present invention (i.e. the catalyst system of the present invention is not used), although the preferred solvent system is employed therein.

It is evident from Table 3 that Examples 20 to 28 give better yields than Examples 29 to 32 and that both Examples 20 to 28 and Examples 29 to 32 give substantially superior yields than Comparative Examples 1 to 3.

TABLE 3

| | Solvent | Catalyst | Yield (%) of trimethylbenzoquinone as measured by gas-chromatography |
|---|---|---|---|
| Example 20 | 5% formic acid-acetic acid | Ru—Ba/C | 91.5 |
| Example 21 | 25% formic acid-acetic acid | Ru/C | 97.9 |
| Example 22 | 50% formic acid-acetic acid | Ru—Ba/C | 93.7 |
| Example 23 | 50% formic acid-acetic acid | Ru/C | 94.4 |
| Example 24 | 1% hydrochloric acid-acetic acid | Ru—Ba/C | 87.4 (Yield when isolated) |
| Example 25 | 1% hydrochloric acid-acetic acid | Ru/C | 96.5 |
| Example 26 | 1% sulfuric acid-acetic acid | Ru—Ba/C | 96.0 |
| Example 27 | 1% sulfuric acid-acetic acid | Ru/C | 98.0 |
| Example 28 | 5% trifluoro acetic acid-acetic acid | Ru/C | 94.0 |
| Example 29 | acetic acid | Ru—Ba/C | 87.3 |
| Example 30 | acetic acid | Ru/C | 76.0 |
| Example 31 | formic acid | Ru—Ba/C | 80.7 |
| Example 32 | 25% propionic acid-acetic acid | Ru—Ba/C | 80.8 |
| Comparative Example 1 | 25% formic acid-acetic acid | /C* | 70.6 |
| Comparative Example 2 | 1% sulfuric acid-acetic acid | /C* | 70.0 |
| Comparative Example 3 | 1% sulfuric acid-acetic acid | —* | 63.7 |

*The reaction times in Comparative Examples 1, 2 and 3 were 27.5 hours, 28.5 hours and 24 hours, respectively.

EXAMPLE 33

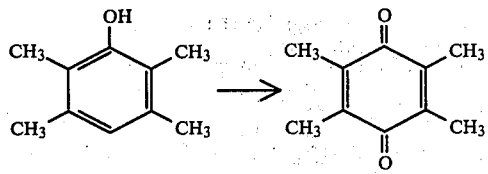

To 30 mg of the catalyst prepared in the same manner as in Example 19, 100 mg of water was added and stirred, and then 5 ml of an acetic acid solution containing 1% of hydrochloric acid was added. While cooling the mixture with water, 500 mg of 2,3,5,6-tetramethylphenol and 1 g of a 31% hydrogen peroxide aqueous solution were added, and the mixture was stirred for 2.5 hours. After the completion of the reaction, the mixture was diluted with ether, and the catalyst was filtered and washed successively with a NaHCO₃ aqueous solution and a saturated sodium chloride aqueous solution. The filtrate was dried over MgSO₄ and then concentrated, and the residue was purified by silica gel chromatography by eluting it with a solvent mixture of hexane-dichloromethane (1:1), whereby 300 mg (55% yield) of tetramethylbenzoquinone was obtained.

EXAMPLE 34

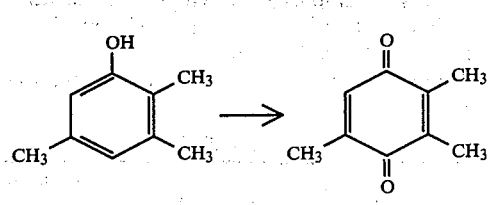

The reaction was conducted for 24 hours in the same manner as in Example 33 except that 2,3,5-trimethylphenol was used as the starting material. After the completion of the reaction, the reaction mixture was diluted with ether and, after adding pentamethylbenzene as an internal standard, analyzed by gas-chromatography, whereby it was found that the conversion was 47% and the yield of trimethylbenzoquinone was 28.8% (i.e. the selectivity: 61.3%). The conditions employed for the gas-chromatography analysis were the same as those given in Example 19.

We claim:
1. A method for preparing a benzoquinone represented by the general formula:

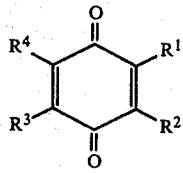 (I)

where each of R¹, R², R³ and R⁴ is a hydrogen atom, an alkyl group or an aryl group, which comprises reacting a phenol represented by the general formula:

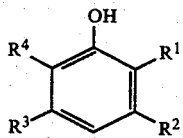 (II)

where R¹, R², R³ and R⁴ are as defined above, with hydrogen peroxide in the presence of a ruthenium catalyst.

2. The method according to claim 1, wherein the ruthenium catalyst is composed of ruthenium chloride, ruthenium bromide, a μ₃-oxotriruthenium complex, a ruthenium phosphine complex or a ruthenium carbonyl complex.

3. The method according to claim 1, wherein the ruthenium catalyst is supported on a carrier together with an alkaline earth metal.

4. The method according to claim 3, wherein the ruthenium catalyst is composed of ruthenium chloride, ruthenium bromide, a μ₃-oxotriruthenium complex, a ruthenium phosphine complex or a ruthenium carbonyl complex, and the alkaline earth metal is magnesium, calcium, strontium or barium.

5. The method according to claim 3, wherein from 0.5 to 20% by weight, based on the carrier, of ruthenium is supported on the carrier together with from 0.02 to 2 equivalent, based on the ruthenium, of the alkaline earth metal.

6. The method according to claim 1, wherein the ruthenium catalyst is supported on a carrier and the reaction is carried out in a medium composed essentially of from 50 to 99.5% by weight of acetic acid and from 0.5 to 50% by weight of another acid having a smaller acid dissociation index (pKa) than acetic acid.

7. The method according to claim 3, wherein the reaction is carried out in a medium composed essentially of from 50 to 99.5% by weight of acetic acid and from 0.5 to 50% by weight another acid having a smaller acid dissociation index (pKa) than acetic acid.

8. The method according to claim 1, wherein 2,3,6-trimethylphenol is reacted with hydrogen peroxide to obtain 2,3,6-trimethylbenzoquinone.

9. The method according to claim 3, wherein 2,3,6-trimethylphenol is reacted with hydrogen peroxide to obtain 2,3,6-trimethylbenzoquinone.

10. The method according to claim 6, wherein 2,3,6-trimethylphenol is reacted with hydrogen peroxide to obtain 2,3,6-trimethylbenzoquinone.

11. The method according to claim 7, wherein 2,3,6-trimethylphenol is reacted with hydrogen peroxide to obtain 2,3,6-trimethylbenzoquinone.

12. The method according to claim 6, wherein said another acid is selected from the group consisting of formic acid, oxalic acid, malonic acid, methoxyacetic acid, chloroacetic acid, dichloroacetic acid, trichloroacetic acid, trifluoroacetic acid, benzoic acid, methanesulfonic acid, benzenesulfonic acid, toluenesulfonic acid, hydrochloric acid and sulfuric acid.

13. The method according to claim 7, wherein said another acid is selected from the group consisting of formic acid, oxalic acid, malonic acid, methoxyacetic acid, chloroacetic acid, dichloroacetic acid, trichloroacetic acid, trifluoroacetic acid, benzoic acid, methanesulfonic acid, benzenesulfonic acid, toluenesulfonic acid, hydrochloric acid and sulfuric acid.

14. The method according to claim 1, wherein the reaction is conducted at a temperature of from 0° to 100° C.

15. The method according to claim 1, wherein the reaction is conducted at a temperature of from 10° to 60° C.

16. The method according to claim 1, wherein the reaction is conducted in a solvent selected from a carboxylic acid or a mixture of a saturated alcohol and a mineral acid.

* * * * *